United States Patent [19]
Gentelia et al.

[11] Patent Number: 5,599,348
[45] Date of Patent: Feb. 4, 1997

[54] ELECTROSURGICAL TROCAR ASSEMBLY

[75] Inventors: John S. Gentelia, Madison; Frank Williams, Frankfort; William C. Wheatley, Utica; Ernesto G. Sevilla, Herkimer; Sharyn Longo, Frankfort; Deborah Forbey, Smyrna, all of N.Y.

[73] Assignee: Conmed Corporation, Utica, N.Y.

[21] Appl. No.: 187,127

[22] Filed: Jan. 27, 1994

Related U.S. Application Data

[63] Continuation of Ser. No. 853,149, Mar. 17, 1992, abandoned.

[51] Int. Cl.⁶ .................................................. A61B 17/32
[52] U.S. Cl. ........................... 606/45; 606/41; 606/42; 604/21; 604/164
[58] Field of Search ........................ 606/32–34, 38–42, 606/45–50, 167, 184; 604/21, 22, 164, 264

[56] References Cited

U.S. PATENT DOCUMENTS

| | | | |
|---|---|---|---|
| 3,359,982 | 12/1967 | Guiorguien | 606/36 |
| 3,595,239 | 7/1971 | Petersen . | |
| 3,812,858 | 5/1974 | Oringer | 606/39 X |
| 4,170,234 | 10/1979 | Graham | 606/45 |
| 4,788,977 | 12/1988 | Farin et al. | 606/39 |
| 4,986,814 | 1/1991 | Burney et al. | 604/164 |
| 5,071,419 | 12/1991 | Rydell et al. . | |
| 5,088,997 | 2/1992 | Delahuerga et al. | 606/45 |
| 5,100,402 | 3/1992 | Fan | 606/45 |
| 5,300,070 | 4/1994 | Gentelia et al. | 606/45 |
| 5,344,420 | 9/1994 | Hilal et al. | 606/16 X |

FOREIGN PATENT DOCUMENTS

| | | | |
|---|---|---|---|
| 1324658 | 7/1987 | U.S.S.R. | 606/45 |
| 14514 | 9/1992 | WIPO | 604/45 |

*Primary Examiner*—Stephen C. Pellegrino
*Assistant Examiner*—Michael Peffley
*Attorney, Agent, or Firm*—Larson and Taylor

[57] ABSTRACT

A trocar assembly includes an elongate trocar device and a surrounding cannula. The trocar device incorporates an electrosurgical cutting element which is used to make a guide hole for the cannula and thus enables the remainder of the trocar assembly to enlarge the puncture. An electronic control circuit senses the current flow to the cutting element and, when the trocar device breaks through the wall of the organ being cut, this circuit cuts off the connection to the associated electrosurgical generator. Further control circuitry prevents a surgeon from resuming electrosurgery until a predetermined time period has elapsed. Multiple trocars of different diameters are provided for the same assembly.

24 Claims, 4 Drawing Sheets

5,599,348

ELECTROSURGICAL TROCAR ASSEMBLY

This application is a continuation of application Ser. No. 07/853,149 filed on Mar. 17, 1992, now abandoned.

FIELD OF THE INVENTION

The present invention relates to trocar devices or assemblies used in surgery and, more particularly, to an electrosurgical trocar device or assembly.

BACKGROUND OF THE INVENTION

Surgical procedures such as laparoscopic procedures require the surgeon to create one or more punctures in the anatomy of the patient to enable a guide tube, referred to as a cannula, to be sited and thereby enable surgical instruments to be passed down through the cannula into the patient in order to carry out the intended procedures.

One method of accomplishing this is the open or "Hussan" method wherein an incision is made in the desired area to accommodate the cannula and sutures are put around the cannula to close the gap left by the incision. Sutures are also made from the skin to cannula to assist in holding the cannula in place. This technique is used primarily (but not exclusively) in situations wherein other abdominal surgeries pose potential adhesion complications. Such complications can cause an unintended puncture in the bowel or in other organs.

A second method involves the use of a mechanical trocar device which comprises the combination of a trocar and a cannula. The trocar basically comprises a rod or shaft having a very sharp cutting edge or point at one end thereof and is enclosed within the tubular cannula. In some devices, the cannula incorporates some kind of safety mechanism, such as a shield, over the cutting tip prior to use to reduce the chance of unintended punctures. Trocar devices characteristically require substantial force to drive the cutting end or tip through the abdomen wall and as a result, trocar devices can be hard to control. A separate trocar device, i.e., comprising a trocar and cannula, is used for each puncture site.

SUMMARY OF THE INVENTION

In accordance with the invention, a trocar device or assembly is provided which overcomes the problems with prior art trocar devices discussed above. The trocar device of the invention comprises an electrosurgical cutting element, which, in common with electrosurgical cutting instruments commonly referred to as electrosurgical "blades," provides cutting of tissue through the transmission of radio frequency electrical energy to the area to be cut. The trocar device of the invention uses electrosurgery to make the guide hole for the cannula and thus enables the remainder of the cannula assembly to enlarge the puncture. This greatly reduces the force required as compared with mechanical trocar devices. This reduction in force enables an even, constant insertion pressure to be exerted, thereby allowing substantially greater control and reducing the chances of an unintended puncture. Further, the use of electrosurgery eliminates the need for a sharp point as is required in mechanical trocar devices, thereby allowing multiple uses of the same trocar.

The electrosurgical cutting element is, in use, connected to a conventional electrosurgical generator or other source of radio frequency (r.f.) power or energy (the term electrosurgical generator being used herein to refer to any suitable source for driving the electrosurgical cutting element), and a further important feature of the trocar assembly of the invention is in the provision of an electronic control circuit for sensing current flow and, when the trocar breaks the wall of the organ involved, for opening or cutting off the connection to the electrosurgical generator. This feature substantially eliminates any chance of an unintended puncture.

In addition, further circuitry is preferably provided which requires that the operator (surgeon) release a control switch for a predetermined time period prior to resuming surgical operations so that power is again provided to the electrosurgical cutting element only as the result of a conscious decision on the part of the operator. As a result, inadvertent operation of the cutting element, and thus possible inadvertent puncturing of the organ wall, are combatted or avoided. Advantageously, an indicator such as a light emitting diode (LED) is used to indicate that the generator is supplying power to the cutting element (preferably by providing a continuous light output) and to also indicate the predetermined time period before electrosurgery can be resumed (preferably by providing a blinking or intermittent light output).

A further important feature of the invention involves the provision of multiple trocars as part of a trocar assembly or kit, independently of whether or not an electrosurgical cutting element is used. The provision of multiple trocars enables the same basic device to provide punctures or openings of different diameters. The trocars can be very simple in construction and thus can be made to be low cost disposable items.

Other features and advantages of the invention will be set forth in, or apparent from, the following detailed description of preferred embodiments of the invention.

DESCRIPTION OF THE PREFERRED EMBODIMENTS

Figure 1:
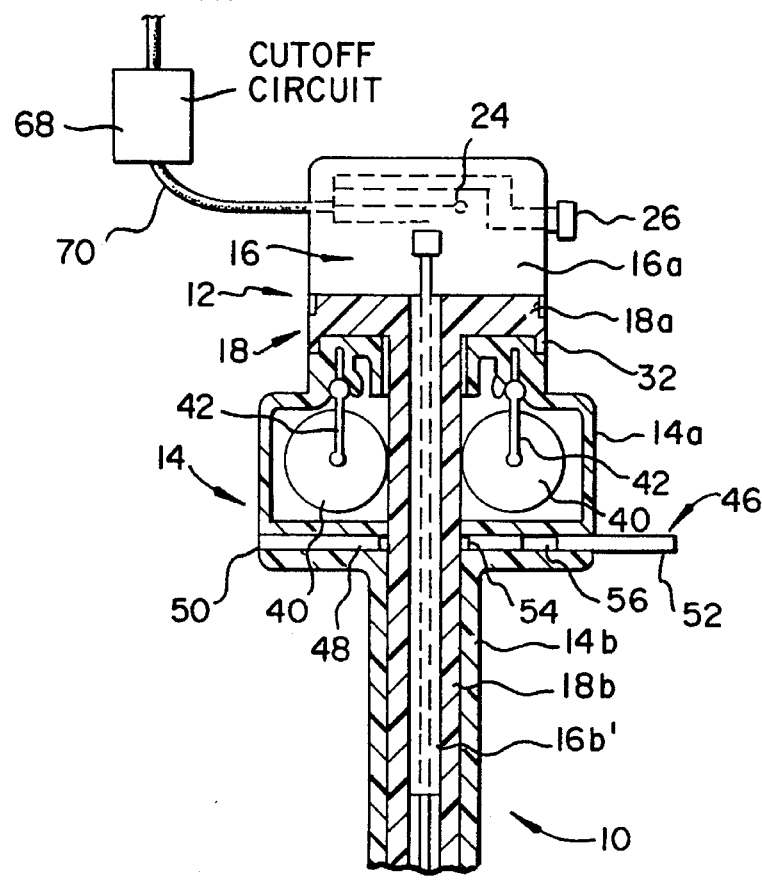
FIG. 1 is a side elevational view, partially in cross section, of a trocar assembly in accordance with a preferred embodiment of the invention.

Referring first to FIG. 1, there is shown a schematic side elevational view, partially in section, of a trocar assembly which is generally denoted 10. The trocar assembly 10 basically comprises a multi-element trocar 12 and a cannula 14.

Figure 5:
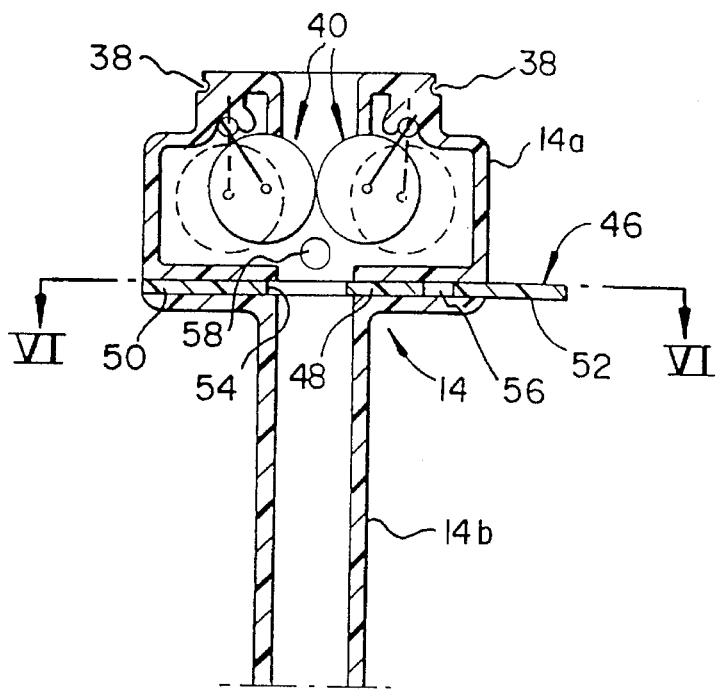
FIG. 5 is a partial cross sectional view of the cannula of the trocar assembly of FIG. 1 showing the operation of the seal rollers.
Figure 6:
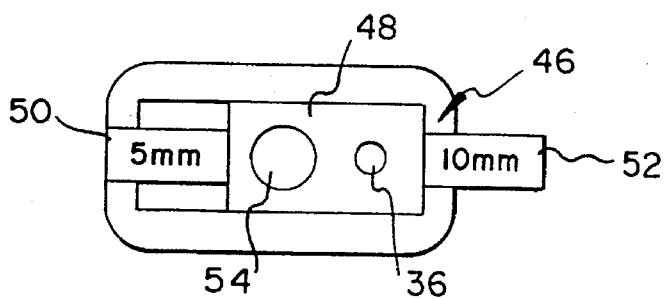
FIG. 6 is a cross sectional view taken generally along line VI—VI of FIG. 5.

The multi-element trocar 12 includes a central or inner trocar member 16 (perhaps best seen in FIGS. 2 and 4) comprising a head portion 16a and a shaft or rod portion 16b, and an outer trocar member 18 (perhaps best seen in FIGS. 3 and 4) which comprises a head portion 18a and a hollow shaft portion 18b and which slides onto and releasably engages trocar member 16. As shown, head portion 18a of trocar member 18 is affixed to head portion 16a while shaft portion 18b surrounds shaft or rod portion 16b. The cannula 14, which is also shown in FIGS. 5 and 6, comprises a head or upper housing portion 14a and a guide tube or cannula portion 14b. As shown, head portion 14a is affixed to the head portion 18a of the outer trocar member 18 and the cannula portion 14b surrounds hollow shaft portion 18a.

Figure 2:
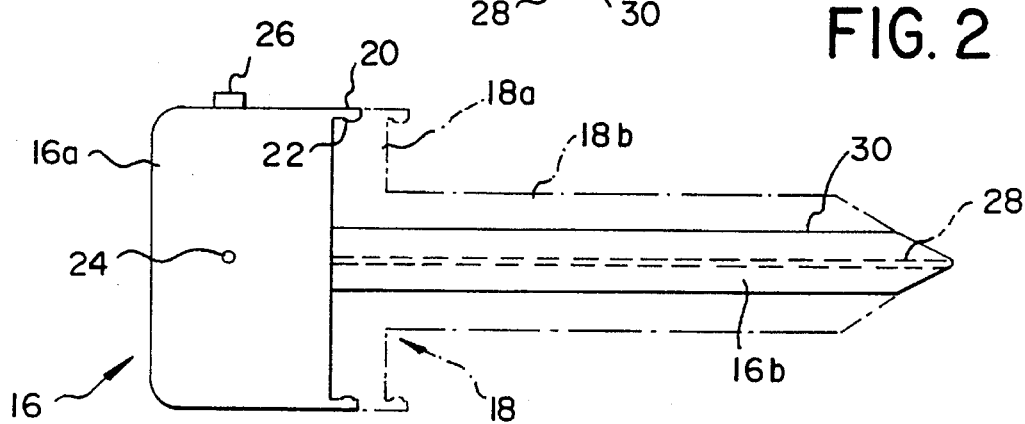
FIG. 2 is a side elevational view of one of the trocars of FIG. 2, with the second trocar being shown in phantom lines.
Figure 3:
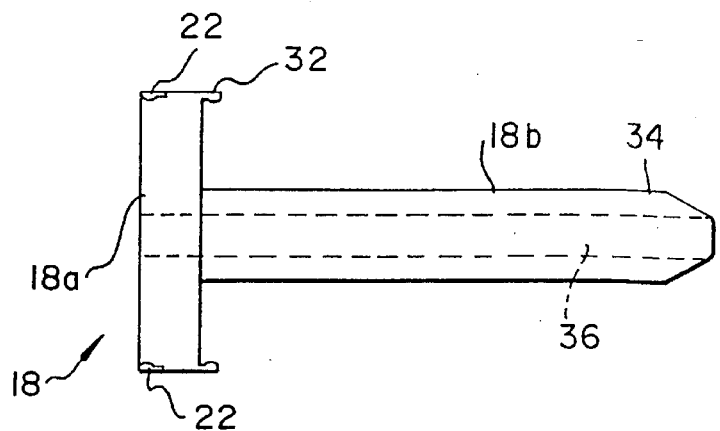
FIG. 3 is a side elevational view of the second, outer trocar of FIG. 1.
Figure 4:
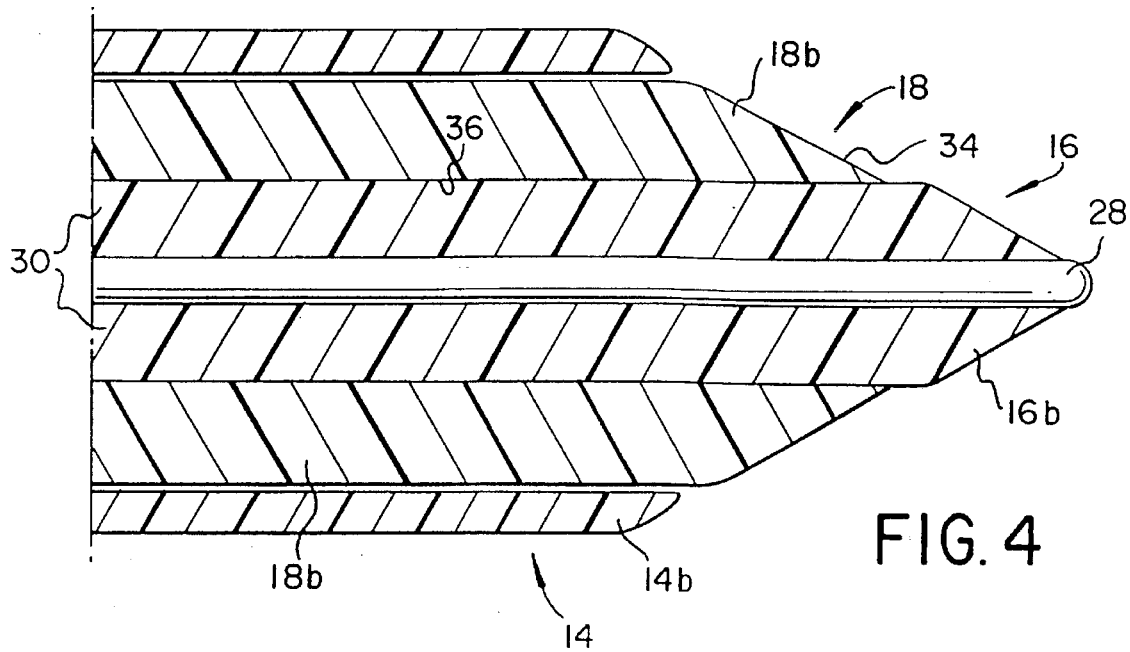
FIG. 4 is a cross section view, to an enlarged scale, of the distal or free end of the trocar assembly of FIG. 1.

Considering the inner or central trocar member 16 in more detail and referring to FIGS. 1, 2 and 4, head portion 16a is generally cylindrical in shape and includes an outwardly extending locking member or skirt 20 having a shaped rim or circumferential lip portion which is adapted to be received in a corresponding recess 22 in head portion 18a of outer trocar 18 (see also FIG. 3) so as to provide a releasable snap fit, as is indicated in phantom lines in FIG. 2. It will be understood that a similar releasable connection can be provided between the trocar members 16 and 18 using other suitable connecting arrangements.

Head portion 16a is also provided with an indicator light or lamp 24 for indicating the operating state of the device as explained below and a reset pushbutton switch 26 which resets the electronic circuitry described below.

The shaft portion 16b of central trocar member 16 comprises a central metal rod 28 and an outer insulating trocar shaft or tube 30. In a specific exemplary embodiment, rod 28 is made of stainless steel and is about 0.075 inches in diameter while trocar shaft 30 is made of a plastic, ceramic or any like material capable of providing the appropriate temperature resistance as well as has a relatively low coefficient of friction and has an outside diameter of about 3/16 of an inch or 5 mm. The distal end of trocar shaft 30 is tapered as illustrated so as to enable ready insertion thereof into a small hole "burned" through the organ wall by rod 28.

Electrical power is provided to rod 28 through an electrical circuit located in head portion 16a and discussed in more detail below in connection with FIG. 7. This circuit, which is also shown in dashed lines in FIG. 1 includes indicator lamp 24 and switch 26.

Referring to FIG. 3, the head portion 18a of the second or outer trocar member 18 is also cylindrical in shape and, as noted above, includes a circumferential recess 22 for receiving locking or latching member 20. A similar locking or latching member or skirt 32 having rim or circumferential lip is provided at the other end of head portion 18a, as shown. The shaft portion 18b comprises a tubular trocar shaft 34 having a central bore 36 therein through which the central trocar shaft 30 extends. The distal end of trocar shaft 34 is tapered and as shown in FIG. 4 (and in FIG. 1), the overall taper provided by trocar shafts 30 and 34 is continuous or substantially continuous. Trocar member 18 does not contain any active components and in an exemplary embodiment has an outside diameter of about 13/32 inches or 10 mm and an inside diameter about 7/32 inches, i.e., a diameter just slightly larger than the outer diameter of inner trocar shaft 30. However, it is to be understood that outer trocar members of different sizes can be used and that a set of such trocar members can be provided which would selectively be slipped onto and over inner trocar shaft 30 to provide openings of different sizes in the wall of the abdomen or other organ. It will be appreciated that such outer trocars, which, as noted above, contain no active parts, are quite simple in construction and inexpensive to manufacture.

Referring now to FIGS. 1, 5 and 6, it will be seen that the head portion 14a of the cannula member 14 is hollow in construction and includes a shaped circumferential recess 38 in the upper or proximal end thereof in which reciprocally shaped circumferential locking member 32 of outer trocar member 18 is received so as to provide a snap fit between members 14 and 18.

Disposed within the head portion 14a of cannula member 14 are a pair of sealing rollers or rolls 40 which are suspended from the upper or proximal end wall of head portion 14a by springs 42 that bias the rolls 40 toward each other so as to close off an opening 44 in that proximal end wall, as shown in solid lines in FIG. 5. Inserting the shaft portions 16b and 18b of trocar members 16 and 18 down into opening 44 causes rolls 40 to be forced apart and to assume the positions shown in FIG. 1 and in dashed lines in FIG. 5. Reference is made to our commonly assigned copending application Ser. No. 07/846,386, filed on Mar. 5, 1992, and entitled LAPAROSCOPIC CANNULA for a further description of arrangement for permitting insertion of a trocar while shutting off the opening for the trocar after the trocar is removed.

A selectable seal device 46 is best seen in FIG. 6. The seal device 46 includes a flat sealing member 48 having pull tabs 50 and 52 at opposite ends thereof and openings 54 and 56 of different sizes so as to accommodate trocars of different diameters. In the exemplary embodiment illustrated, the openings 54 and 56 are designed to receive the 10 mm trocar 18 and the 5 mm trocar 16 and tabs 50 and 52 are marked accordingly. Thus, with 10 mm tab 52 pulled out so that sealing member 48 is moved to the right as shown in FIG. 6, the 10 mm opening 54 is brought into alignment or registration with opening 44 so that the 10 mm outer diameter trocar 16 can be inserted therethrough as indicated in FIG. 1. Sealing member 48 is disposed in a slot in housing portion 18a and is slidable therein as described above. It will be appreciated that the embodiment just described is exemplary only and that, for example, the openings in sealing member 46 can be different in number and sizes so as to accommodate surgical instruments of various sizes during surgery.

As shown in FIG. 5, an opening 58 is provided in head or housing portion 14a which enables irrigation fluid to be supplied to the puncture site through cannula shaft 14b, when the trocars 16 and 18 are removed.

Figure 7:
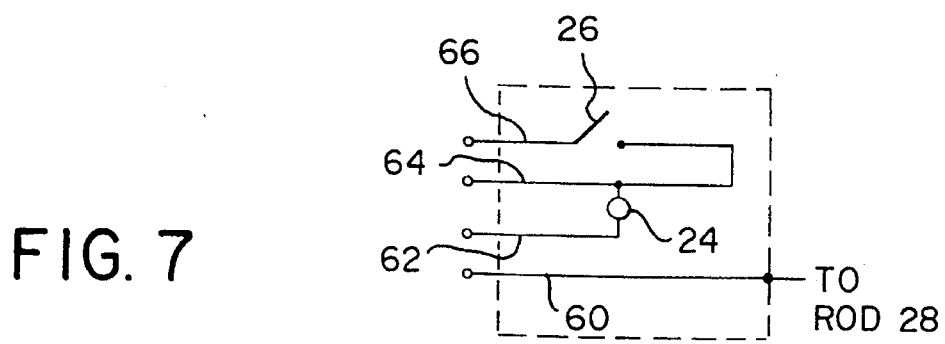
FIG. 7 is a schematic circuit diagram of circuitry incorporated into the cannula of FIG. 1.

Referring to FIG. 7, there is shown a schematic circuit diagram of the electrical circuitry contained within the head portion 16a of the main trocar 16 (this circuitry also being shown in dashed lines in FIG. 1). As illustrated, four input leads or connections, denoted 60, 62, 64, and 66 are provided, one of which, lead 60 is the "hot" lead directly connected to electrosurgical rod 28. Leads 64 and 66 provide a current input and return path for switch 26 while lead 62 connects optional indicator lamp 24 to lead 64.

Figure 8:
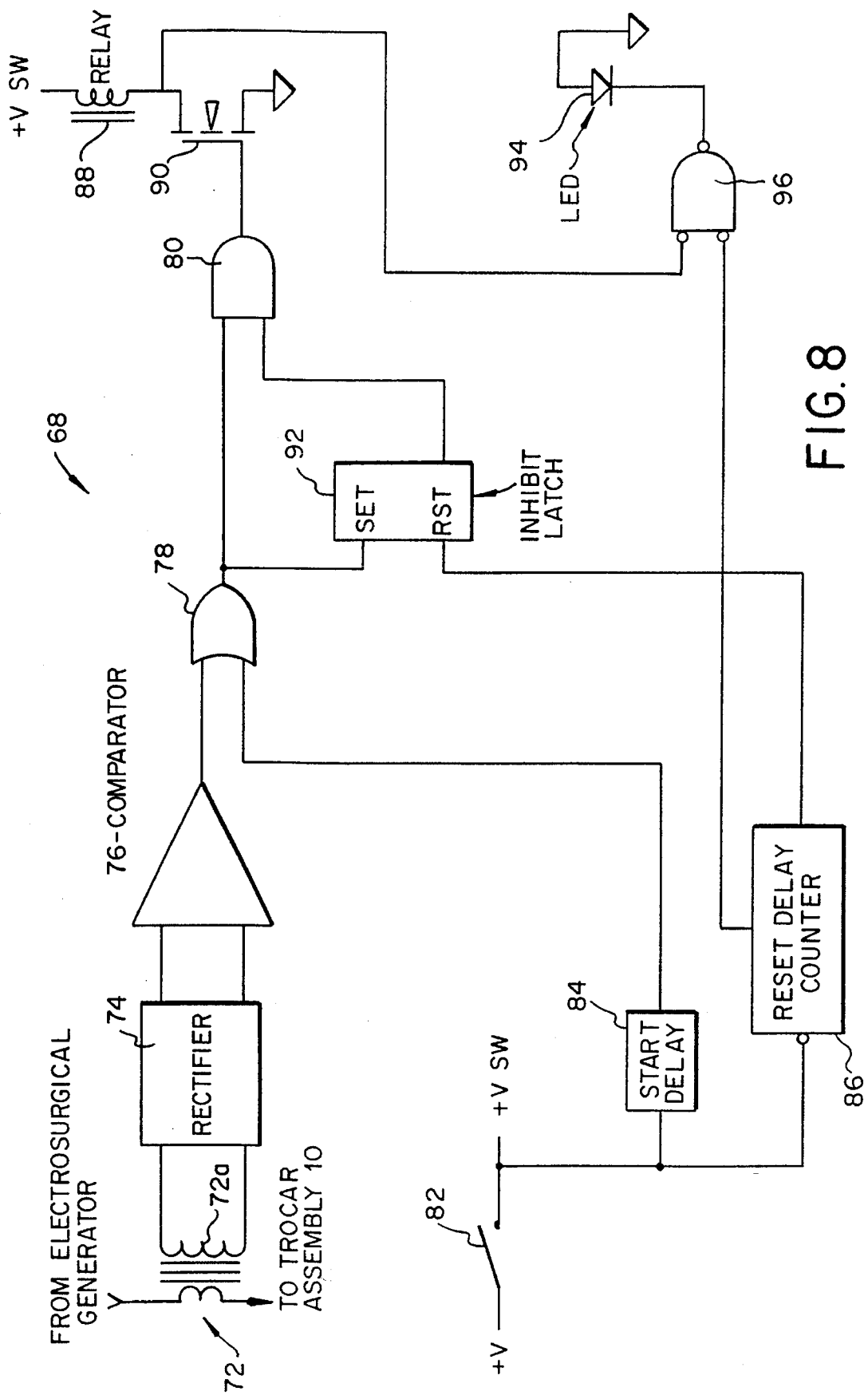
FIG. 8 is a schematic circuit diagram of the cutoff circuit of FIG. 1.

Referring to FIG. 8, a preferred embodiment of the cutoff circuit for the electrosurgical generator is shown. As indicated in FIG. 1, the cutoff circuit, which is generally denoted 68, can be a separate package or unit connected into the cable 70 or in another connection between the electrosurgical generator (not shown) and the trocar assembly 10. Alternatively, the circuit can be built into the electrosurgical generator. The cutoff circuit 68 of FIG. 8 includes a current transformer 72 connected to the generator output line (which can correspond to cable 70 of FIG. 1) so as to sense or monitor the current flow from the electrosurgical generator (not shown) to the trocar assembly 10. The secondary winding 72a of transformer 72 is connected to a rectifier 74 which produces an output voltage that is a function of the current level. Rectifier 74 is connected to an adjustable voltage comparator 76 which determines the cutoff current by comparing the output voltage produced by rectifier 74 with a predetermined reference level. The output of comparator 76 is connected to one input of an OR gate 78 the output of which is connected to an AND gate 80. The functions of the gates 78 and 80 are described in more detail below.

A control switch 82 is provided for controlling energizing of the electrosurgical generator. This switch can correspond to switch 26 described above and is controlled by the surgeon. A pair of delay networks, a start delay circuit 84 and a reset delay counter circuit 86, are connected to switch 82 in parallel with each other. Start delay circuit 84 begins timing out its associated delay when switch 82 is closed while reset delay counter circuit 86 begins timing out its associated delay when switch 82 is opened. The significance of delay circuits 84 and 86 is explained below.

The output of start delay circuit 84 is connected to the other input of OR gate 78 and the delay provided allows time for the surgeon to start a cut after activating the switch 82. Thus, when switch 82 is closed the output of start delay circuit 78 provides for closing of a control relay 88 for the electrosurgical generator so as to turn on the electrosurgical generator. Relay 88 is connected to the output of AND gate 80 through an IGFET switch 90 provided so as to ensure that the appropriate relay switching levels are maintained. After delay circuit 84 times out, the operation of relay 88 is controlled by the output of the current sensor 72 and, more particularly, by the output of comparator 76. Thus, if this output drops below the level set within comparator 76, relay 88 is opened and power to the electrosurgical generator is cut off.

The cutoff circuit 68 also includes an inhibit latch 92 which includes a first, set input connected to the output of OR gate 78, a second, reset input connected to the output of reset delay counter circuit 86 and an output connected to the other input of AND gate 80. When the sensed current drops below the preset or predetermined reference value dictated by comparator 76, this is reflected at the set input of inhibit latch 90 and latch 90 is set (in addition to the control relay 88 opening as mentioned above). The inhibit latch 90 will remain set until the switch 82 is opened for the reset delay period, i.e., the period of reset delay counter circuit 86, which is approximately three seconds in a specific exemplary embodiment. The reason for this provision is that the normal current level will drop when an initial puncture is made and the intention here is to ensure that the electrosurgical cutting element rod 28 will not be used to cut again until the surgeon intentionally provides for the electrosurgical generator to be turned back on, i.e., after the three second delay provided by reset delay counter circuit 86. As noted above, opening of switch 82 starts the inhibit or reset delay period, and during this delay period it is not possible to turn the generator on. In this regard, reactivating switch 82 resets the delay period, so that in order to turn on the electrosurgical generator, switch 82 must be released or opened, and left open for the full delay period, in order to reset the inhibit latch circuit 92. Of course, with inhibit latch 92 reset, the circuit operates as set forth above and the surgeon can begin cutting again.

In order to alert the surgeon to the fact that the reset delay period is being timed out, an intermediate stage of the counter of the reset delay counter circuit 86 is used to cause an indicator light or lamp (e.g., a LED) 94 to blink during the inhibit delay period. (Again, indicator lamp 94 can correspond to indicator lamp 24 of FIG. 1.) Considering this operation in more detail, a negative OR or NOR gate 94 is provided which has a first input connected to the output of IGFET switch 90, a second input connected to the aforementioned intermediate stage of reset delay counter 86 and the output connected to the LED 94. When the output of switch 90 is low, meaning that control relay 88 is actuated and the electrosurgical generator is turned on, LED 94 will also be continuously on to provide an indication to the surgeon that the generator is on. Further, as set forth above, when the generator is off but the reset delay period is being timed out, the intermediate stage of reset delay counter 86 will provide a pulsed signal to NOR gate 96 which will cause blinking of LED 94 during this period. As explained previously, when this period is up, as indicated by the fact that LED 94 is no longer blinking, the surgeon will know that he can close switch 82 and resume surgery.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A trocar assembly comprising a first trocar comprising a first elongate trocar shaft, of a first outer diameter, including a first tapered surface at the distal end and an electrosurgical cutting element comprising a central conductive rod extending along the longitudinal axis of the first shaft, said rod terminating in a distal end extending beyond said first tapered surface and being adapted to be connected to an electrosurgical generator; and a second trocar comprising a second elongate hollow trocar shaft of a second, larger outer diameter, having a distal end comprising a second tapered surface, and including a longitudinal bore in which, in use, the first trocar shaft of the first trocar is received in nested relation; and a cannula including a longitudinal bore in which, in use, both the first and second trocar shafts can be received.

2. A trocar assembly as claimed in claim 1 wherein said first trocar includes a first head portion at the proximal end of said first trocar shaft, said second trocar includes a second head portion at the proximal end of said second trocar shaft, and said first and second head portions include means for detachably connecting said head portions together so as to detachably affix said first and second trocars to one another.

3. A trocar assembly as claimed in claim 1 wherein said cannula further comprises means, comprising an elongate slide member having openings of different diameters along the length thereof, for providing sealing between the cannula and trocars of different diameters.

4. A trocar system comprising a trocar device including an electrosurgical cutting element having a distal end, a cannula surrounding said trocar device, means for connecting said cutting element of said trocar device to an electrosurgical generator for supplying power to said cutting element, and sensing means for sensing an electrical parameter which varies in response to penetration of at least a part of said cutting element through the wall of a body cavity of a patient undergoing electrosurgery and for, responsive to a variation in said parameter indicative of said penetration, interrupting the power supplied to the cutting element by the electrosurgical generator.

5. A trocar assembly as claimed in claim 4 wherein said sensing means comprises a sensor for sensing a change in load impedance in response to said penetration.

6. A trocar assembly as claimed in claim 5, wherein said sensor comprises a current sensor for sensing the current flow from the electrosurgical generator to the cutting element of the trocar device and for interrupting the power supplied to the cutting element by the electrosurgical generator responsive to the sensed current falling below a preset level.

7. A trocar assembly comprising a trocar device including an electrosurgical cutting element adapted to be connected to an electrosurgical generator, a control switch for, in a first position thereof, providing completion of a connection between the electrosurgical generator and the electrosurgical cutting element and for, in a second position thereof, providing interruption of said connection, and circuit means for, responsive to interruption of said power by said control switch, preventing power from being supplied to said electrosurgical cutting element during a predetermined time period independently of whether said control switch is in the first position thereof.

8. A trocar assembly comprising: an elongate trocar device and a cannula surrounding said trocar device, said trocar device comprising an electrosurgical cutting element comprising a central conductive rod extending longitudinally of said trocar device and terminating in a distal end and being adapted to be connected to an electrosurgical generator, a first insulating trocar shaft secured to said rod and having a longitudinal bore therein in which said rod is received so that the distal end of said rod is exposed, the end of said first trocar shaft adjacent to said distal end being tapered, and a further, separate trocar shaft received within said cannula and having a bore therein in which the first trocar shaft is received, said further trocar shaft having a tapered end and the tapered end of said further trocar shaft and the tapered end of the first trocar shaft forming a substantially continuous taper.

9. A trocar assembly comprising: an elongate trocar device and a cannula surrounding said trocar device, said trocar device comprising an electrosurgical cutting element comprising a central conductive rod extending longitudinally of said trocar device and terminating in a distal end and being adapted to be connected to an electrosurgical generator, a first insulating trocar shaft secured to said rod and having a longitudinal bore therein in which said rod is received so that the distal end of said rod is exposed, the end of said first trocar shaft adjacent to said distal end being tapered, and a further, separate trocar shaft received within said cannula and having a bore therein in which the first trocar shaft is received, said trocar device further comprising a first head portion connected to said first trocar shaft and a further head portion connected to said further trocar shaft, and said first and further head portions being detachably connected together.

10. A trocar assembly as claimed in claim 9 wherein said trocar assembly further comprises means for connecting said cutting element of said trocar device to an electrosurgical generator for supplying power to said cutting element, sensing means for sensing an electrical parameter associated with the operation of the electrosurgical generator, and control means, connected to said sensing means, for interrupting the power supplied to the cutting element by the electrosurgical generator when the sensed parameter varies from a preset level in response to a portion of the distal end of the cutting element entering a body cavity of a patient undergoing electrosurgery.

11. A trocar assembly comprising an elongate trocar device and a cannula surrounding said trocar device, said trocar device comprising an electrosurgical cutting element comprising a rod terminating in a blunt distal end, said cutting element being adapted to be connected to an electrosurgical generator, and said trocar assembly further comprising a control switch for, in a first position thereof, providing completion of a connection between the electrosurgical generator and the electrosurgical cutting element and for, in a second position thereof, providing interruption of said connection, and circuit means for, responsive to interruption of said power by said control means, preventing power from being supplied to said electrosurgical cutting element during a predetermined time period independently of whether said control switch is in the first position thereof.

12. A trocar assembly as claimed in claim 11 further comprising indicator means for producing a first indication when power is supplied to said electrosurgical cutting element and a second indication during said predetermined time period.

13. A trocar assembly as claimed in claim 11 wherein said circuit means includes a delay counter circuit for timing out said predetermined time period responsive to said control switch being switched to the second state thereof.

14. A trocar assembly as claimed in claim 11 wherein said circuit means comprises a reset delay counter actuated responsive to said control switch being switched to said second state thereof so as to time out said predetermined time period and a latching circuit, which is set responsive to said sensing means and which is reset responsive to said reset delay counter after said predetermined time period, for, when reset, enabling power to be supplied to said cutting element when said control switch is switched to said first state thereof.

15. A trocar assembly as claimed in claim 14 wherein said sensing means includes a current transformer for sensing said current level and for producing an output in accordance therewith and a control relay, responsive to the output of said current transformer and to said latching circuit, for turning said electrosurgical generator on and off.

16. A trocar assembly as claimed in claim 15 wherein said reset delay counter includes an intermediate stage and said trocar assembly further comprises a light emitting diode connected to said control relay and to said intermediate stage of said counter for producing a continuous light signal when said control relay turns said generator off and for producing a blinking light signal during said predetermined time period.

17. A trocar assembly as claimed in claim 11 further comprising means responsive to initial switching of said control switch to the first state thereof for providing that said power is supplied to said cutting element from said electrosurgical generator during a further predetermined time period independently of the output of said sensing means.

18. An electrosurgical trocar assembly comprising a cannula and a trocar device disposed within said cannula, said trocar device comprising a central, longitudinally extending, cylindrical conductive rod of a first diameter terminating in a blunt distal end of gradually decreasing diameter from said first diameter, an insulating trocar shaft surrounding said rod and providing a surface of a tapered profile; means for connecting said rod to a source of radio frequency power so that said rod can be used to perform electrosurgery; and control means for interrupting the supply of said radio frequency power from said source to said rod in response to puncturing of a wall of a cavity of a patient upon whom electrosurgery is being performed.

19. A trocar assembly as claimed in claim 18 further comprising circuit means for preventing an operator from resuming electrosurgery after interruption of said power by said control means until a control switch for controlling the supply of said power by said source is opened and permitted to remain open for a predetermined delay period.

20. A trocar assembly as claimed in claim 18 wherein said trocar assembly further comprises means for connecting said cutting element of said trocar device to an electrosurgical generator for supplying power to said cutting element, and sensing means for sensing an electrical parameter which varies in response to penetration of at least a part of the distal end of the cutting element through the wall of a body cavity of a patient undergoing electrosurgery and for, responsive to a variation in said parameter indicative of said penetration, interrupting the power supplied to the cutting element by the electrosurgical generator.

21. A trocar assembly as claimed in claim 20 wherein said sensing means comprises a sensor for sensing a change in load impedance in response to said penetration.

22. A trocar assembly as claimed in claim 21, wherein said sensor comprises a current sensor for sensing the current flow from the electrosurgical generator to the cutting element of the trocar device and for interrupting the power supplied to the cutting element by the electrosurgical generator responsive to the sensed current falling below a preset level.

23. A trocar assembly as claimed in claim 20 further comprising an indicator means for indicating when power is being supplied to said cutting element by said electrosurgical generator.

24. A trocar assembly as claimed in claim 23 wherein said indicator means comprises a light indicator device for producing a light output when power is supplied to said cutting element by said electrosurgical generator.

* * * * *